United States Patent [19]

Yasuda et al.

[11] 4,303,613
[45] Dec. 1, 1981

[54] GAS SENSING APPARATUS

[75] Inventors: Eturo Yasuda, Okazaki; Minoru Ohta, Anjo, both of Japan

[73] Assignee: Nippon Soken, Inc., Nishio, Japan

[21] Appl. No.: 127,490

[22] Filed: Mar. 5, 1980

[30] Foreign Application Priority Data

Mar. 15, 1979 [JP] Japan .................................. 54-30804

[51] Int. Cl.$^3$ ...................... G01N 27/04; G01N 27/16
[52] U.S. Cl. ...................... 422/95; 73/27 R; 324/71 SN; 338/22 SD; 422/98; 123/440
[58] Field of Search .................. 123/440, 489, 589; 422/95, 98; 338/22 SD, 34; 73/27 R; 324/71 SN

[56] References Cited

U.S. PATENT DOCUMENTS

| | | | |
|---|---|---|---|
| 4,112,893 | 9/1978 | Anzai ................................ | 123/440 |
| 4,147,513 | 4/1979 | Bienkowski et al. ............ | 338/34 X |
| 4,149,502 | 4/1979 | Johnson et al. .................. | 123/440 |
| 4,208,786 | 6/1980 | Merchant et al. ............... | 338/22 SD |

Primary Examiner—Michael S. Marcus
Attorney, Agent, or Firm—Cushman, Darby & Cushman

[57] ABSTRACT

A gas sensing apparatus for sensing the air-fuel ratio in an internal combustion engine has two sinter elements fixed to the tip of a tubular ceramic body and both of the sinter elements are made of metal oxide which exhibits an electrical resistance change in response to changes in the component and temperature of the exhaust gas. One of the sinter elements carries a catalyst to promote the oxidation reaction of the gas component and the other sinter element which does not carry a catalyst and connected in series to the one sinter element serves for temperature compensation of the electrical resistance change of the one sinter element. A fixed resistor having a resistance value considerably smaller than that of the other sinter element not carrying a catalyst at low exhaust gas temperature is connected in parallel with the other sinter element to maintain the apparent resistance of the other sinter element at small values at the low exhaust gas temperature.

4 Claims, 6 Drawing Figures

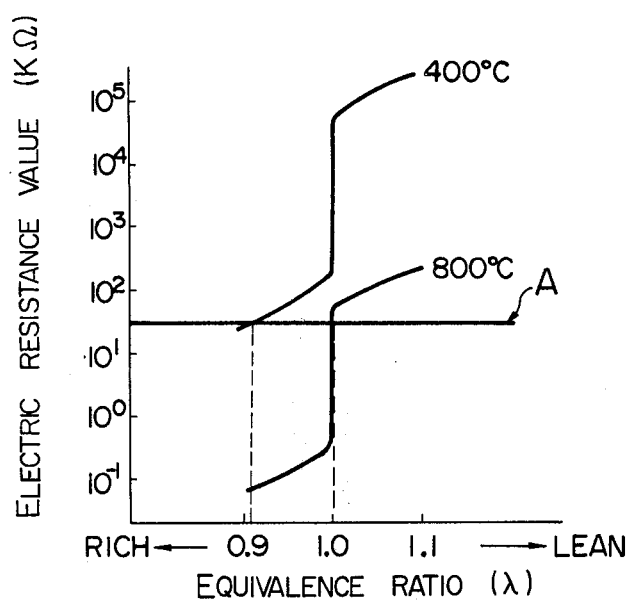
FIG. I
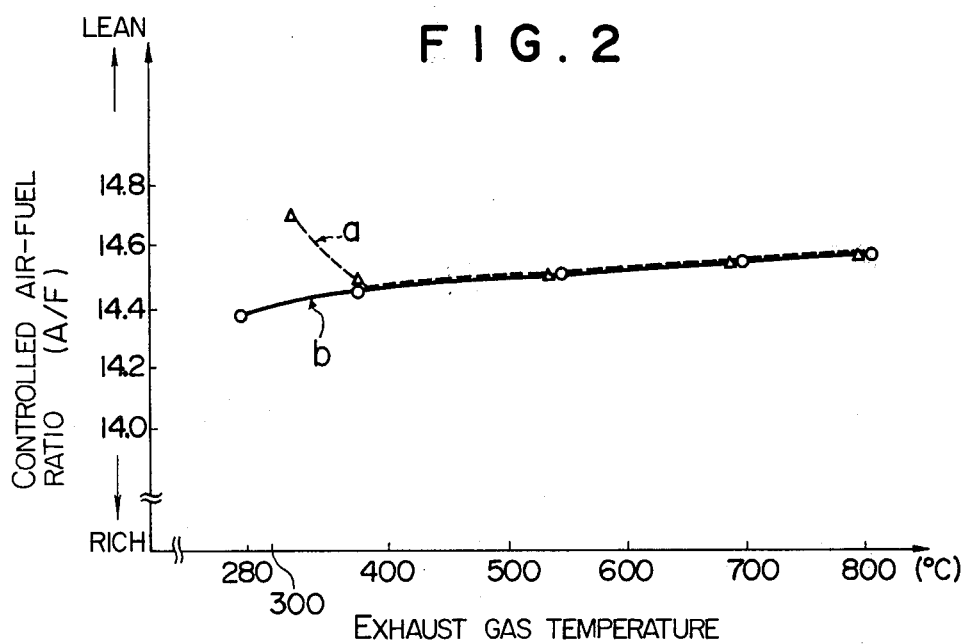
FIG. 2

GAS SENSING APPARATUS

BACKGROUND OF THE INVENTION

The present invention relates to a gas sensing apparatus adapted to be incorporated, for example, in an internal combustion engine exhaust emission control system employing a three-way catalyst so as to sense the air-fuel ratio.

Sensors for sensing the air-fuel ratio of internal combustion engines are known in the art which employ a transition metal oxide responsive to the composition of the exhaust gases so as to detect changes in the electric resistance value of the oxide.

As shown in FIG. 1 of the accompanying drawings, the electric resistance value of the transition metal oxide varies depending not only on the atmosphere of the exhaust gases, that is, whether the equivalence ratio $\lambda$ ($\lambda$ = actual air-fuel ratio/stoichiometric air-fuel ratio) is smaller than 1, i.e., rich or greater than 1, i.e., lean but also on the exhaust gas temperature. Thus there is a disadvantage that while, if the exhaust gas temperature is 800° C., it is possible to sense the equivalence ratio $\lambda$ at a reference value corresponding to that shown by a solid line A and thereby to control the factor at around $\lambda = 1$ (stoichiometric air-fuel ratio), if the exhaust gas temperature is 400° C., the equivalence ratio $\lambda$ can be sensed only on the considerably rich side compared with around $\lambda = 1$ as shown in FIG. 1 so that it will be made impossible to control the air-fuel ratio and consequently it will be made impossible to properly control the air-fuel ratio unless compensation for changes in the electric resistance caused by the exhaust gas temperatures or temperature compensation is provided.

To overcome the foregoing deficiencies, another type of gas sensing apparatus such as disclosed in West German Document Open For Inspection No. 2817873 has been proposed in which the sensing apparatus comprises a pair of sinters made of metal oxide having an electric resistance value which varies with both the relative atmosphere and the exhaust gas temperature, only one of the sinters having deposited thereon a gas composition oxidizing catalyst, and a change in the electric resistance value of the catalyst deposited sinter (catalytic element) is sensed while subjecting the catalytic element to temperature compensation by the other sinter having no catalyst (non-catalytic element), thereby sensing electric resistance value changes which are not affected by the exhaust gas temperatures and are dependent only on the relative atmosphere and accurately controlling the air-fuel ratio.

The air-fuel ratio control system employing the sensing apparatus of this prior art is disadvantageous in that while the air-fuel ratio can be controlled at a considerably wide range of temperatures from 360° C. to over 800° C. as shown by a dotted line a (marked with $\Delta$) in FIG. 2, any attempt to effect the control even at temperatures as low as about 280° C. will control the air-fuel ratio to the lean side or result in an improper control. This is considered to be due to the fact that the resistance of the non-catalytic element becomes as high as over 10 megaohms and the resulting disturbance such as noise appearing on the signal line cannot be completely eliminated or prevented by an electric circuit or the like.

SUMMARY OF THE INVENTION

With a view to overcoming the foregoing deficiencies, it is the object of this invention to provide an improved gas sensing apparatus in which a fixed resistor is connected in parallel with a non-catalytic element whereby when the resistance value of the non-catalytic element increases extraordinarily at low exhaust gas temperatures of about 280° C., the resistance value is apparently prevented from increasing by the fixed resistor making it possible for example to satisfactorily sense the air-fuel ratio of the exhaust gases in relation to the stoichiometric ratio as a reference at such low exhaust gas temperatures.

In accordance with the invention, by virtue of the fact that a fixed resistor is connected in parallel with a non-catalytic element or second sinter, even if the resistance value of the non-catalytic element increases extraordinarily at low exhaust gas temperatures of about 280° C., the apparent resistance value is prevented from increasing by the fixed resistor thus making it possible for example to satisfactorily sense the air-fuel ratio on the basis of the stoichiometric ratio even at such low exhaust gas temperatures.

BRIEF DESCRIPTION OF THE DRAWINGS

FIGS. 1 and 2 are characteristic diagrams useful for explaining the present invention and the prior art.

DESCRIPTION OF THE PREFERRED EMBODIMENTS

The invention will now be described in greater detail with reference to the illustrated embodiments.

Figure 3:
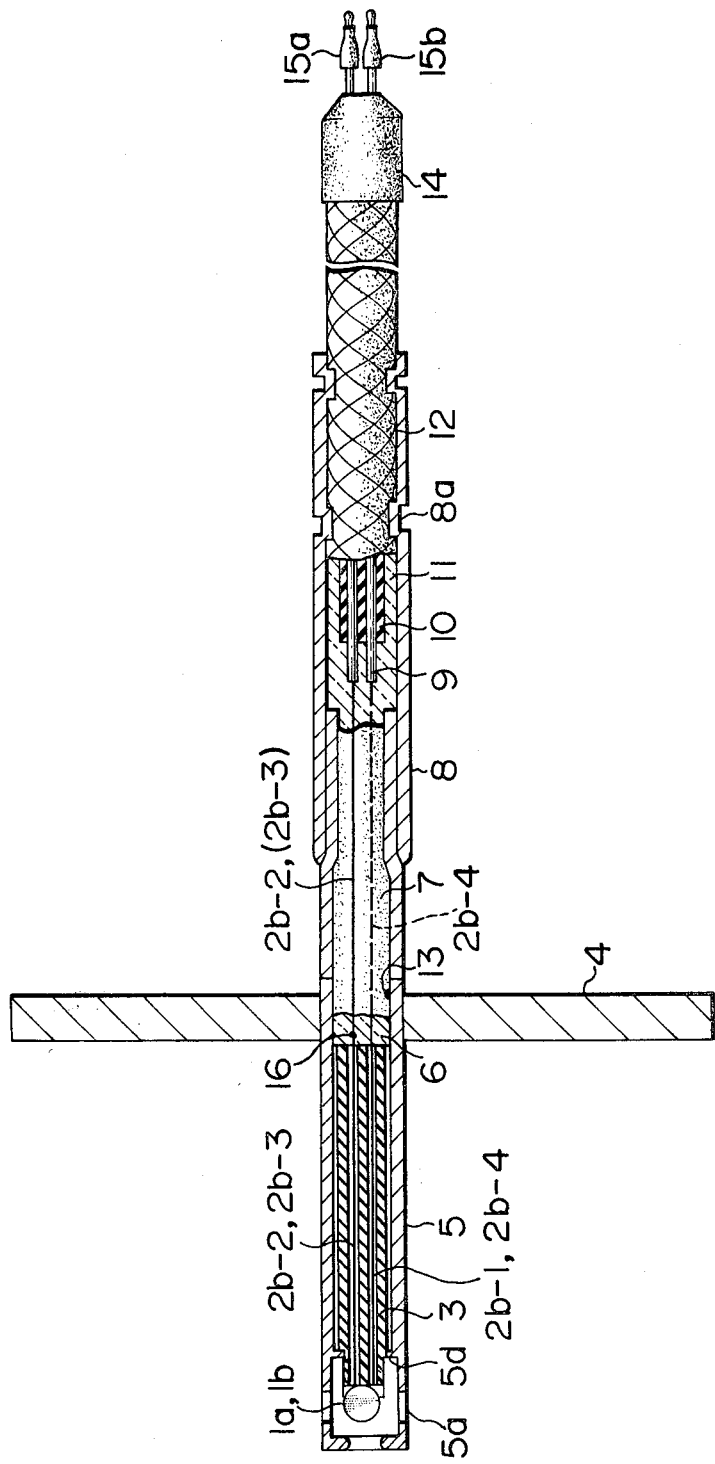
FIG. 3 is a sectional view showing the construction of an embodiment of the invention.
Figure 4:
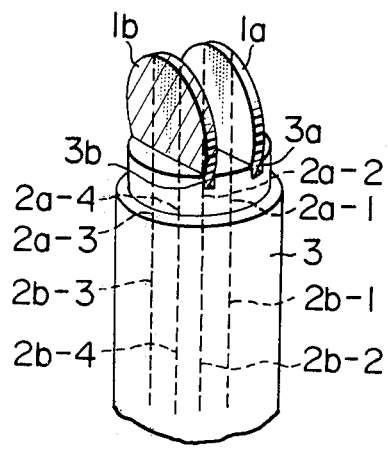
FIG. 4 is a perspective view of the principal part of FIG. 3.

Referring first to FIGS. 3 and 4 showing the overall construction of a gas sensor according to an embodiment of the invention, numeral 1a designates a disk sensing element (non-catalytic element) consisting of a metal oxide or titania ($TiO_2$) sinter (second sinter), 1b another disk sensing element (catalytic element) consisting of a similar metal oxide or titania sinter (first sinter) having a catalyst deposited thereon), 2a-1, 2a-2, 2a-3 and 2a-4 electrodes made of platinum or the like and embedded in the sensing elements 1a and 1b, 2b-1, 2b-2, 2b-3 and 2b-4 sublead wires made of heat resisting metal such as nichrome wires welded respectively to the electrodes 2a-1 to 2a-4 so as to be electrically connected for communication therewith, and 3 a tubular ceramic member formed therethrough with four small holes of the same diameter into which are respectively inserted the electrodes 2a-1 to 2a-4 and the sublead wires 2b-1 to 2b-4, the ceramic member 3 being made of a heat resisting and electrically insulating ceramic such as alumina. The ceramic member 3 is formed at its forward end with two slots 3a and 3b and the sensing elements 1a and 1b are fixedly fitted in these slots. This construction is effective in firmly fixing the sensing elements in place and the construction also serves the purpose of making the electrodes 2a-1 to 2-a4 thinner.

Numeral 4 designates a flange made of a heat resisting metal and adapted for mounting the sensor to the exhaust pipe. Numeral 5 designates a heat resisting metal pipe having a plurality of holes 5a for introducing the exhaust gases therethrough with the flange 4 being fixedly mounted thereon and formed in the lower end portion thereof is an annular projection 5d on which is mounted the ceramic member 3. Numeral 6 designates a hardened glass sealer placed between the ceramic member 3 and the pipe 5 to fill in the opening of the holes through the ceramic member 3. The glass sealer 6 provides sealing against the exhaust gases and also ensures insulation and fixing of the sublead wires 2b-1 to 2b-4. Numeral 7 designates powder of alumina, magnesia or the like used to fix in place and electrically insulate the sublead wires 2b-1 to 2b-4 from each other. Numeral 9 designates a pair of lead wires respectively connected by welding to the sublead wires 2b-2 and 2b-4 for communication therewith. A cover 10 made of a heat resisting and electrically insulating material such as glass wool or heat resisting rubber is externally placed around the lead wires 9 and another cover 11 of the same material is placed around the cover 10, thus electrically insulating the lead wires 9 from each other. Numeral 12 designates a knitted cover of heat resisting metal which is externally placed around the cover 11. The cover 12 is fastened to a pipe 8 by caulking the end portion of the latter as shown at numeral 8a. The sublead wires 2b-2 and 2b-3 respectively associated with the electrodes 2a-2 and 2a-3 are welded at a point 16 and the sublead wire 2b-1 associated with the electrode 2a-1 is welded at a point 13 to the pipe 5 forming a housing. Numeral 14 designates a heat shrinkable tubing, and 15a and 15b connecting terminals connected to the lead wires 9.

Figure 5:
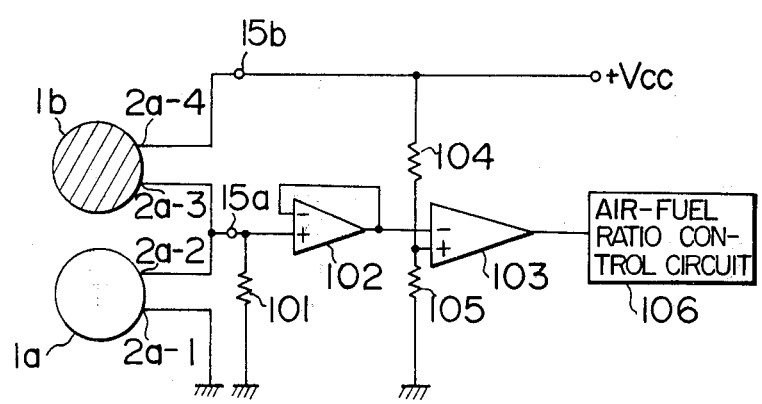
FIG. 5 is a circuit diagram showing by way of example the circuit construction of an air-fuel ratio control system incorporating the gas sensor shown in FIG. 3.

Referring to FIG. 5 showing by way of example an electric circuit of an engine air-fuel ratio control system incorporating the above-described gas sensor, a fixed resistor 101 of about 2 MΩ in this embodiment is connected in parallel with non-catalytic element 1a or between the ground and the terminal 15a connected to the electrode 2a-2. The resistance value of the resistor 101 should preferably be in the range of about 1.5 to 3 MΩ, although it is dependent on the element 1a. A fixed voltage $V_{cc}$ of about 8 volts is applied to the other terminal 15b or the electrode 2a-4 of the catalytic element 1b. Numeral 102 designates a current amplifier for amplifying the gas sensor output from the terminal 15a, and 103 a comparator for comparing the gas sensor output with a comparison reference value (about 6 volts in this embodiment) determined by resistors 104 and 105 so as to determine whether the air-fuel ratio is great (lean) or small (rich) as compared with a predetermined (stoichiometric) air-fuel ratio. The output of the comparator 103 is supplied to a known type of air-fuel ratio control circuit 106.

With the construction described above, the operation of the system is as follows. When the temperature of the exhaust gases is low so that the gas sensor ambient temperature is on the order of 280° C., the resistance value of the non-catalytic element 1a is increased to several tens of MΩ. While, in the case of the prior art sensor, this gives rise to a problem that the stoichiometric air-fuel ratio point of the exhaust gases cannot be sensed due to electric noise, for example, making it impossible to accurately control the air-fuel ratio, in this system the parallel fixed resistor 101 of about 2 MΩ is connected so that during the periods of such high resistance the level at the output terminal 15a is determined by the resistance value of the fixed resistor 101. Consequently, when the air-fuel ratio is lean, the level at the output terminal 15a decreases below the comparison reference value determined by the resistors 104 and 105, that is, the level goes across the comparison reference value without fail and thus the air-fuel ratio can be sensed on the basis of the stoichiometric air-fuel ratio. On the other hand, when the exhaust gas temperature rises to a high temperature of over 300° C., the resistance value of the non-catalytic element 1a becomes very low as compared with that of the parallel fixed resistor 101 so that the fixed resistor 101 can be ignored and the air-fuel ratio can be sensed on the basis of the stoichiometric air-fuel ratio as in the case of the prior art sensor.

Figure 6:
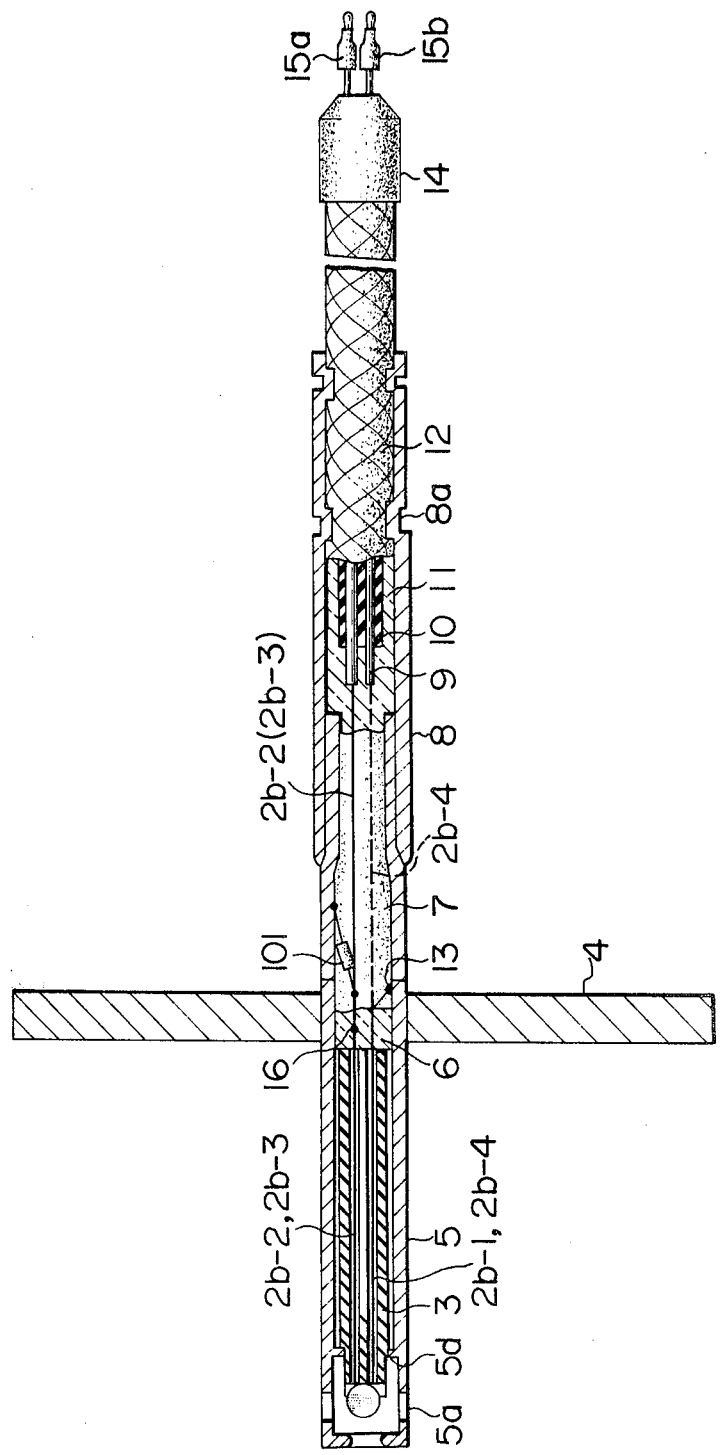
FIG. 6 is a sectional view showing the construction of another embodiment of the invention.

While, in the embodiment described above, the parallel fixed resistor 101 is provided on the circuit side, the fixed resistor 101 may be provided on the gas sensor side as in the case of another embodiment of the invention shown in FIG. 6. In the embodiment of FIG. 6, the fixed resistor 101 is connected to the welded sublead wire 2b-2 (2b-3) and the body grounded pipe 5.

We claim:
1. A gas sensing apparatus having:
a first sinter formed from a metal oxide having an electric resistance value which varies in accordance with the composition and temperature of a gas to be sensed, said first sinter having supported thereon a catalyst adapted to promote oxidation reaction of components of said gas;
a second sinter formed from a metal oxide having an electric resistance value which varies in accordance with the composition and temperature of said gas to be sensed; said second sinter having supported thereon no catalytic material similar to said catalyst;
said first and second sinters having electrodes therein and being arranged in association with each other so that said gas is sensed while compensating by said second sinter for changes in the electric resistance value of said first sinter with temperature; and
a single fixed resistor permanently connected in parallel electric circuit relation with said second sinter, the resistance value of said single fixed resistor being significantly smaller than the resistance value of said second sinter at a low temperature of said gas thereby rendering a voltage developed across said second sinter primarily governed by the resistance value of said single fixed resistor, and with the resistance value of said second sinter being significantly smaller than the resistance value of said fixed resistor in a temperature range above said low temperature of said gas thereby rendering the voltage developed across said second sinter as primarily governed by the resistance value of said second sinter.

2. A gas sensing apparatus according to claim 1 further comprising a tubular, electrically insulating ceramic body having two slots formed in one end thereof, and wherein said first and said second sinters are disc shaped and are fixed in said two slots respectively.

3. A gas sensor for sensing the components contained in an exhaust gas from an internal combustion engine and for determining an equivalence ratio of an air-fuel mixture supplied to the engine having:
a pipe-shaped casing, a tubular, electrically insulating ceramic body provided in said pipe-shaped casing, first and second sinter elements fixed to one end of said ceramic body and being spaced apart from each other, said first sinter element being made of titania carrying at least on a surface thereof a catalyst for promoting oxidating reaction of the gas components, an electric resistance value of said first sinter element being varied depending on the gas components and exhaust gas temperature, and said second sinter element being made of substantially only titania, an electric resistance value of said second sinter element being varied depending primarily on the exhaust gas temperature, a plurality of electrodes connected to said first and second sinter elements for taking out electrically the changes in the electric resistance values of said first and second sinter elements, and a single fixed resistor permanently connected in parallel electric circuit relation with said second sinter element, the resistance value of said single fixed resistor being significantly smaller than the resistance value of said second sinter element at a low temperature of said gas thereby rendering a voltage developed across said second sinter element primarily governed by the resistance value of said single fixed resistor, and with the resistance value of said second sinter element being significantly smaller than the resistance value of said single fixed resistor in a temperature range above said low temperature of said gas thereby rendering the voltage developed across said second sinter element as primarily governed by the resistance value of said second sinter element.

4. A gas sensor according to claim 3 wherein said tubular ceramic body has two slots formed in one end thereof and said first and second sinter elements formed in a disc shape are respectively fixed in said two slots.

* * * * *